United States Patent [19]

Castelijns et al.

[11] Patent Number: 5,811,588

[45] Date of Patent: Sep. 22, 1998

[54] PROCESS FOR THE PREPARATION OF 3-PHENYLPROPANAL

[75] Inventors: Anna M. C. F. Castelijns, Beek; Johanna M. Hogeweg, Sittard; Simon P. J. M. van Nispen, Beek, all of Netherlands

[73] Assignee: DSM N.V., Heerlen, Netherlands

[21] Appl. No.: 834,456

[22] Filed: Apr. 16, 1997

[30] Foreign Application Priority Data

Oct. 17, 1994 [NL] Netherlands ............................. 9401708

[51] Int. Cl.⁶ .................................................... C07C 45/62
[52] U.S. Cl. ............................ 568/434; 562/408; 562/415
[58] Field of Search .............................. 568/434; 562/408, 562/415

[56] References Cited

U.S. PATENT DOCUMENTS 3,520,934   7/1970   Dunkel et al. .

FOREIGN PATENT DOCUMENTS 2 030 031   12/1971   Germany .
955421      1/1964    United Kingdom .

Primary Examiner—Gary Geist
Assistant Examiner—Sreeni Padmanabhan
Attorney, Agent, or Firm—Pillsbury, Madison & Sutro LLP; Cushman Darby & Cushman Intellectual Property Group

[57] ABSTRACT

Process for the preparation of 3-phenylpropanal in which cinnamaldehyde is hydrogenated with the aid of a Pd-containing catalyst in the presence of a small amount of water. A high yield and a high selectivity are obtained in a commercially attractive process. The reaction mixture obtained can without intermediate further processing be subjected to an oxidation in which the cinnamaldehyde is oxidized to 3-phenylpropionic acid with a high degree of conversion and a high selectivity. The combination of the two process steps constitutes a simple, commercially attractive process for the preparation of 3-phenylpropionic acid using cinnamaldehyde as a starting material. The resulting 3-phenyl-propionic acid product may serve as an intermediate reagent in the synthesis of anti-viral pharmaceuticals, particularly HIV protease inhibitors.

16 Claims, No Drawings

PROCESS FOR THE PREPARATION OF 3-PHENYLPROPANAL

This is a continuation of International Appln. No. PCT/NL95/00359 filed Oct. 17, 1995 which designated the U.S.

BACKGROUND OF THE INVENTION

1. Field of the Invention

The invention relates to a process for the preparation of 3-phenylpropanal in which cinnamaldehyde is hydrogenated with the aid of a Pd-containing catalyst.

Such a process is known from DE-A-2030031, which describes a process with which a (substituted) cinnamaldehyde is hydrogenated with the aid of a $Pd/Al_2O_3$ catalyst, under conditions that are essentially free of water. Good results are obtained with the hydrogenation of p-t.butyl-α-methyl cinnamaldehyde. The results obtained with the hydrogenation of non-substituted cinnamaldehyde are not reported. In general, as is for example apparent from NL-A-6613916, the yield and selectivity obtained with the hydrogenation of non-substituted cinnamaldehyde are considerably poorer than those obtained with substituted cinnamaldehydes.

The hydrogenation of (substituted) cinnamaldehyde using a Pd/C catalyst, in the presence of an aqueous basic solution of an alkali compound, i.e. in a two-phase system, is known, for example from NL-A-7703007 and NL-A-6613916. Such a two-phase system presents the advantages in this type of hydrogenation that the formation of byproducts such as cinnamic alcohol is suppressed and the yield is increased. A drawback of a two-phase system, however, is that, due to the presence of an aqueous solution, the production capacity is much lower and, moreover, an additional separation step is necessary. Such a process is hence commercially less attractive.

SUMMARY OF THE INVENTION

The invention provides a process for the hydrogenation of cinnamaldehyde to 3-phenylpropanal with which, in a commercially attractive process, 3-phenylpropanal is obtained with a high yield and a high selectivity.

DETAILED DESCRIPTION OF THE INVENTION

The production of 3-phenylpropanal from cinnamaldehyde is achieved according to the invention by carrying out the hydrogenation in the presence of 1–5 wt. % water, relative to the amount of cinnamaldehyde.

With the process according to the present invention both a high production capacity and a high yield and high selectivity are realised in the hydrogenation of cinnamaldehyde to 3-phenylpropanal.

The temperature at which the process according to the invention is carried out is not critical and is usually around ambient temperature or an elevated temperature, for example of between 20° and 180° C. Preferably a temperature of between 55° and 90° C. is used because it seems that the highest selectivity can then be obtained. The pressure at which the process according to the invention is carried out is not critical either. Usually use is made of atmospheric or an elevated pressure, for example a pressure of between 0.1 and 15 MPa. Preferably the hydrogenation is carried out at a pressure of between 0.5 and 8 MPa, in particular between 4 and 8 MPa.

Preferably Pd on a carrier is used as the Pd-containing catalyst, for example a Pd/C or a $Pd/Al_2O_3$ catalyst. The amount of catalyst to be used is not critical. Mostly use is made of between 0.01 and 2 wt. % Pd, preferably between 0.01 and 0.5 wt. % Pd, relative to the amount of cinnamaldehyde.

The selectivity of the hydrogenation can be further increased by adding an alkali salt of a weak acid to the reaction mixture. It has been found that the potassium salt in particular considerably increases the selectivity. Acids with pKa values of 4 or more are suitable for use as the weak acid, for example carbonic acid or carboxylic acids, in particular acetic acid, propionic acid and butyric acid. The best results were obtained by adding potassium acetate.

The reaction mixture obtained after the hydrogenation, which contains mainly 3-phenylpropanal, can, after the removal of the catalyst, be subjected as such, directly, to an oxidation, in which 3-phenylpropionic acid is obtained. It has been found that it is possible to convert 3-phenylpropanal into 3-phenylpropionic acid via a simple oxidation using a medium containing molecular oxygen, for example air, optionally without using a solvent or a catalyst. In this way an extremely simple and commercially attractive process is obtained for the preparation of 3-phenylpropionic acid using cinnamaldehyde as a starting material. To obtain a pure end product in this process it suffices to solely purify the end product—for example through distillation or crystallisation; no intermediate further processing of the hydrogenation mixture is required.

The invention hence also relates to the preparation of 3-phenylpropionic acid via the hydrogenation of cinnamaldehyde to 3-phenylpropanal, followed by the oxidation of 3-phenylpropanal to 3-phenylpropionic acid.

A route via cinnamic acid which is converted into 3-phenylpropionic acid via hydrogenation is often followed for the preparation of 3-phenylpropionic acid in the known processes. This route is technically less attractive because cinnamic acid has to be isolated as a solid substance; the route is also commercially less attractive because of the higher cost price of cinnamic acid.

The oxidation is preferably carried out at an elevated temperature. The temperature is preferably between 40° and 80° C. The temperature is chosen to be as high as possible to obtain the highest possible reaction rate; however, it has been found that the selectivity of the oxidation reaction decreases at higher temperatures. Preferably the temperature is therefore chosen to be between 50° and 70° C., in particular between 55° and 65° C. The pressure at which the oxidation is carried out is not critical and is mostly between approximately atmospheric pressure and 5 MPa. Preferably the oxidation is carried out at elevated pressure, in particular between 0.2 and 2 MPa. In practice it is often simpler to retain a high oxygen concentration in the reaction mixture at an elevated pressure. For obtaining a good result in the oxidation it is of course important to ensure that the reaction mixture contains sufficient oxygen. The optimum conditions for the reaction are hence for example a suitable combination of the amount of oxygen supplied, the degree of mixing of the oxygen in the reaction mixture and the pressure at which the reaction takes place. A person skilled in the art will easily be able to determine the optimum combination for his situation.

The oxidation can optionally be carried out in the presence of a solvent that is inert under the reaction conditions. Examples of suitable solvents are water, aliphatic or aromatic hydrocarbons, in particular hexane, toluene or petroleum ether, or ethers, in particular methyl-t-butylether (MTBE). Preferably the oxidation is carried out without using a solvent, because then the production capacity is greatest and the further processing is simplest.

An oxidation catalyst may optionally also be added. Preferably, however, the oxidation is carried out without a catalyst, because then a simpler process, without catalyst removal, is obtained.

The 3-phenylpropionic acid obtained can be used as an intermediate in the preparation of a number of end products such as pharmaceuticals, in particular, after conversion into the corresponding acid chloride, in the preparation of HIV protease inhibitors, known for example as L-735,524, as described in Tetrahedron Letters, Vol. 33, No. 3, 673–676, J. Med. Chem. 1992, 35, 1685–1701 and Chemistry & Engineering News, May 16, 1994, 6-7.

The invention will be further elucidated with reference to the following examples, without however being limited thereto.

EXAMPLE I 79.5 g of cinnamaldehyde (CALD), 0.19 g of potassium acetate (PAC), 0.8 g of water and 1.86 g of 5% Pd/C (Johnson Matthey type 487; 57.2% $H_2O$ w/w) were dosed to an inertised reactor with a volume of 160 ml, fitted with a turbine stirrer and a hydrogen dosage pipe. The reactor was then brought to a pressure of 58 bar with stirring (with the aid of hydrogen), after which the temperature was raised to 60° C. The pressure was maintained at 50 bar by constantly supplying $H_2$ gas during the reaction. After a reaction time (t) of approximately 5.5 hours virtually no more hydrogen was absorbed. The reactor contents were then cooled to room temperature, after which the reactor was made pressureless and was purged with $N_2$. After the removal of the catalyst through filtration the reaction mixture was analysed by means of gas chromatography. The results are presented in Table 1.

EXAMPLES II–V

Examples II–V were carried out in the same way as described for Example I. The reaction conditions and results are shown in Table I.

EXAMPLE VI 60 kg of cinnamaldehyde, 0.144 kg of potassium acetate and 0.6 kg of $H_2O$ were successively introduced into an inertised Buss-loop reactor with a volume of 50 liters. Then the circulation pump was started and 1.01 kg of 5.2% Pd/C (Johnson Matthey type 487; 54.0% $H_2O$) was dosed, after which the temperature was raised to 65° C., while the pressure was simultaneously raised to 50 bar with the aid of hydrogen. The pressure was kept at 50 bar by constantly supplying $H_2$ gas during the reaction. After approximately 3 hours virtually no more hydrogen was absorbed. The reactor contents were then cooled to room temperature, the pressure was released and the reactor was drained with the aid of $N_2$. After the catalyst had been removed through filtration the reaction mixture was analysed by means of gas chromatography. The results are shown. in Table 1.

EXAMPLES VII–X

Examples VII–X were carried out in the same way as described for Example VI. The reaction conditions and results are shown in Table 1.

COMPARATIVE EXPERIMENTS 1–4

The comparative experiments 1–4 were carried out in the same way as described for Example I. The reaction conditions and results are shown in Table 1.

EXAMPLE XI

The oxidation was carried out in a reactor with a volume of 200 liters, fitted with a stirrer, a gas inlet pipe and a condenser. 143.44 kg of 'crude' phenylpropanal, obtained by mixing two hydrogenation batches obtained according to the procedure described in Example VIII and one hydrogenation batch obtained according to the procedure described in Example IX, was introduced into this reactor. This crude product had the following composition: 93.0 wt. % 3-phenylpropanal, 2.6 wt. % 3-phenylpropanol and 0.9 wt. % $H_2O$.

Then the dosage of air at a flow rate of 73.2 $m^3/h$ (15° C./1 bar) was started, with stirring, and the pressure in the reactor was set to 5 bar. The reaction mixture was then heated to 60° C. and kept at this temperature. The percentage of $O_2$ in the off-gas was originally 15–16% and gradually increased after 4 hours' reaction. After 7.4 hours' reaction virtually no more oxygen was absorbed and the gas flow was stopped and the mixture was cooled to room temperature. The reaction mixture now weighed 154.7 kg; GLC analysis showed that it had the following composition: 3.2 wt. % 3-phenylpropanal, 0.7 wt. % 3-phenylpropanol, 0.5 wt. % cinnamaldehyde; 85.1 wt. % 3-phenylpropionic acid; 0.74 wt. % ethylbenzene and 0.44 wt. % $H_2O$. This corresponds to a degree of conversion of 3-phenylpropanal of 96.3% and a selectivity towards 3-phenylpropionic acid of 91.6%.

TABLE 1

| Exp. No. | Cat.[1] | % Cat.[2] | % $H_2O$[3] added (w/w) | % $H_2O$[3] total (w/w) | % KAC[2] | T(°C.) | p(bar) | t(hr) | degree of conv. of CALD (%) | sel. towards PPAL[3,4] (%) | sel. towards PPOL[3,4] (%) | sel. towards CALC[3,4] (%) |
|---|---|---|---|---|---|---|---|---|---|---|---|---|
| I | 1 | 1 | 1 | 2.34 | 0.24 | 60 | 50 | 5.5 | 100 | 92.3 | 4.3 | 0.7 |
| II | 1 | 1 | 0 | 1.34 | 0.24 | 60 | 50 | 6.75 | 100 | 85.1 | 5.7 | 0.7 |
| III | 1 | 1 | 1 | 2.34 | 0 | 60 | 50 | 5.0 | 97.6 | 79.8 | 14.5 | n.b. |
| IV | 1 | 1 | 1 | 2.34 | 0.24 | 30–40 | 50 | 5.66 | 99.7 | 83.7 | 11.9 | 2 |
| V | 2 | 1 | 1.57 | 1.57 | 0 | 22–84 | 40–50 | 1.75 | 99.7 | 85.9 | 11.0 | n.b. |
| VI | 3 | 0.774 | 1 | 1.91 | 0.24 | 65 | 50 | 3.25 | 99.8 | 91.1 | 5.5 | 0.3 |
| VII | 3 | 0.61 | 1 | 1.72 | 0.24 | 75 | 50 | 2.83 | 99.7 | 93.3 | 3.1 | 0.6 |
| VIII | 3 | 0.61 | 1 | 1.72 | 0.24 | 85 | 50 | 2.1 | 99.4 | 93.5 | 2.4 | 0.6 |
| IX | 3 | 0.61 | 1 | 1.72 | 0.24 | 90 | 50 | 1.73 | 99.5 | 92.9 | 2.8 | 0.5 |
| X | 3 | 0.61 | 1 | 1.72 | 0.24 | 85 | 60 | 1.63 | 99.4 | 94.0 | 3.0 | 0.2 |
| 1 | 1 | 1 | 10 | 11.32 | 0.24 | 60 | 50 | 5.25 | 99.5 | 80.0 | 17.1 | 0.7 |
| 2 | 1 | 1 | 10 | 11.32 | 0 | 60 | 50 | 4.33 | 93.8 | 70.0 | 23.2 | |
| 3 | 1 | 1 | 10 | 11.32 | 0.28 | 30–40 | 50 | 3.25 | 100 | 69.3 | 26.0 | 1.8 |
| 4 | 1 | 5 | 0.9 | 7.56 | 0 | 60 | 50 | 5.63 | 100 | 66.2 | 28.8 | |

TABLE 1-continued

| Exp. No. | Cat.[1] | % Cat.[2] | % H$_2$O[3] added (w/w) | % H$_2$O[3] total (w/w) | % KAC[2] | T(°C.) | p(bar) | t(hr) | degree of conv. of CALD (%) | sel. towards PPAL[3,4] (%) | sel. towards PPOL[3,4] (%) | sel. towards CALC[3,4] (%) |
|---|---|---|---|---|---|---|---|---|---|---|---|---|

[1]cat-1: Johnson Matthey type 487; 57,2% H$_2$O (w/w); 5% Pd/C
cat-2: Degussa E213XR/D; 0% H$_2$O (w/w); 5% Pd/Al$_2$O$_3$
cat-3: Johnson Matthey type 487; 54,0% H$_2$O (w/w); 5,2% Pd/C
[2]% cat. (excl. water) relative to CALD (w/w)
[3]relative to CALD
[4]PPAL = 3-phenylpropanal
PPOL = 3-phenylpropanol
CALC = cinnamic alcohol

What is claimed is:

1. A process for the preparation of 3-phenylpropanal, wherein cinnamaldehyde is hydrogenated with the aid of a Pd-containing catalyst, such that 1–5 wt. % water, relative to the amount of cinnamaldehyde, is present in the reaction mixture during the reaction.

2. The process according to claim 1, wherein the hydrogenation is carried out in the presence of potassium acetate.

3. The process according to claim 1 or claim 2, wherein the hydrogenation is carried out at a temperature of between 55° and 90° C.

4. The process according to claim 1, wherein the hydrogenation is carried out at a pressure of between 4 and 8 MPa.

5. The process for the preparation of 3-phenylpropionic acid, wherein cinnamaldehyde is converted into 3-phenylpropanal according to claims 1, after which the 3-phenylpropanal obtained is subjected to an oxidation using a medium containing molecular oxygen.

6. The process according to claim 5, wherein the oxidation takes place at a pressure between 0.2 and 2 MPa.

7. The process according to claim 5 or claim 6, wherein the oxidation takes place at a temperature between 50° and 70° C.

8. The process according to claim 6, wherein the oxidation is carried out in the absence of a solvent.

9. The process according to claim 5, wherein the oxidation is carried out in the absence of a catalyst.

10. The process for the preparation of an HIV protease inhibitor, wherein 3-phenylpropionic acid is prepared using the process according to claims 5, 6 or 9 and thereafter is converted into said HIV protease inhibitor.

11. The process for preparing an intermediate reagent, wherein 3-phenylpropionic acid obtained according to claim 5 is converted to its corresponding acid chloride.

12. The process according to claim 5, wherein the oxidation takes place at temperatures between 50° C. and 70° C. in the absence of a catalyst.

13. The process according to claim 12, wherein the oxidation is conducted at a pressure of between 0.2 and 2 Mpa.

14. The process according to claim 12, wherein the hydrogenation of cinnamaldehyde occurs in the presence of potassium acetate.

15. The process according to claim 14, wherein the hydrogenation is conducted at a temperature of between 55° C. and 90° C.

16. The process for the preparation of the antiviral pharmaceutical, an HIV protease inhibitor, wherein 3-phenylpropionic acid made according to claims 5, 6 or 9 is used as an intermediate reagent in the synthesis.

* * * * *

UNITED STATES PATENT AND TRADEMARK OFFICE
CERTIFICATE OF CORRECTION

PATENT NO. : 5,811,588
DATED : September 22, 1998
INVENTOR(S) : CASTELIJNS et al.

It is certified that error appears in the above-identified patent and that said Letters Patent is hereby corrected as shown below:

<u>ON THE COVER PAGE:</u>

Please add:

--Related U.S. Application Data

[63] Continuation of international application number PCT/NL95/00359 filed October 17, 1995--

Signed and Sealed this

Eleventh Day of May, 1999

Attest:

Q. TODD DICKINSON

*Attesting Officer*  *Acting Commissioner of Patents and Trademarks*